United States Patent
Maletic

(10) Patent No.: US 11,278,234 B2
(45) Date of Patent: Mar. 22, 2022

(54) SYSTEM AND METHOD FOR NEUROFEEDBACK TRAINING THAT UTILIZES ANIMAL IN THE FEEDBACK LOOP

(71) Applicant: UMO NEUROSCIENCE d.o.o., Zagreb (HR)

(72) Inventor: Marin Maletic, Zagreb (HR)

(73) Assignee: UMO NEUROSCIENCE D.O.O., Zagreb (HR)

( * ) Notice: Subject to any disclaimer, the term of this patent is extended or adjusted under 35 U.S.C. 154(b) by 39 days.

(21) Appl. No.: 16/754,292

(22) PCT Filed: Oct. 2, 2018

(86) PCT No.: PCT/EP2018/076729
§ 371 (c)(1),
(2) Date: Apr. 7, 2020

(87) PCT Pub. No.: WO2019/072626
PCT Pub. Date: Apr. 18, 2019

(65) Prior Publication Data
US 2020/0305752 A1 Oct. 1, 2020

(30) Foreign Application Priority Data
Oct. 13, 2017 (HR) .............................. P20171555A

(51) Int. Cl.
*A61B 5/375* (2021.01)
*A61B 5/00* (2006.01)

(52) U.S. Cl.
CPC ............ *A61B 5/375* (2021.01); *A61B 5/0006* (2013.01); *A61B 5/6801* (2013.01); *A61B 5/7225* (2013.01); *A61B 2503/40* (2013.01)

(58) Field of Classification Search
CPC ........... A61B 5/378; A61B 5/38; A61B 5/381; A61B 5/369; A61B 5/375; A61B 5/0006;
(Continued)

(56) References Cited

U.S. PATENT DOCUMENTS

| | | | | |
|---|---|---|---|---|
| 9,042,201 | B2* | 5/2015 | Tyler | ...................... G06F 3/015 367/139 |
| 2004/0088164 | A1* | 5/2004 | Perlo | .................... A01K 15/021 704/259 |
| 2016/0077547 | A1* | 3/2016 | Aimone | ............... A61B 5/0022 345/8 |
| 2016/0240098 | A1* | 8/2016 | Shin | ........................ G06F 3/015 |
| 2017/0042439 | A1 | 2/2017 | Yeow et al. | |

FOREIGN PATENT DOCUMENTS

| | | |
|---|---|---|
| CN | 104049979 A | 9/2014 |
| WO | WO 2009/102345 A1 | 8/2009 |
| WO | WO 2015/035058 A1 | 3/2015 |
| WO | WO 2016/139576 A2 | 9/2016 |

OTHER PUBLICATIONS

Esposito, L., McCune, S., Griffin, J.A. and Maholmes, V. (2011), Directions in Human-Animal Interaction Research: Child Development, Health, and Therapeutic Interventions. Child Development Perspectives, 5: 205-211. (Year: 2011).*

(Continued)

*Primary Examiner* — Sean P Dougherty
*Assistant Examiner* — Jonathan E. Cooper
(74) *Attorney, Agent, or Firm* — Xsensus LLP

(57) ABSTRACT

The invention discloses a method of operating a system for neurofeedback (NFB) that includes trained animal in a feedback chain. Feedback chain consists of the following steps:

A→B→C→D→A wherein said steps are:
A. real time recording of the subject's EEG performed by the user module and forwarded to the mobile module;
B. analytics of the recorded signal performed by the mobile module and algorithmic decisioning about the stimulation form;

(Continued)

C. forwarding the stimulation towards the animal by using of one or more ultrasonic speakers simultaneously wherein the information needed for the animal performance is forwarded in the form of a coded ultrasonic signal; and D. performing of a learned action by the animal triggered by the received ultrasonic signal from the step C which provides a stimulus to the subject exposed to the NBF training.

10 Claims, 8 Drawing Sheets

(58) Field of Classification Search
CPC . A61B 5/6801; A61B 5/7225; A61B 2503/40; A61B 5/006; A61B 5/291; A61B 5/486; H04B 11/00; G06F 3/015; G10K 5/02; A01M 29/18; A01K 15/02; A01K 15/021; A01K 27/009; A01K 15/022; A01K 15/023; G10H 2240/211
See application file for complete search history.

(56) References Cited

OTHER PUBLICATIONS

International Search Report and Written Opinion dated Jan. 21, 2019 in PCT/EP2018/076729 filed Oct. 2, 2018.

International Preliminary Report on Patentability dated Oct. 15, 2019 in PCT/EP2018/076729 filed Oct. 2, 2018.

Cheol-Hu Kim, et al., "Remote Navigation of Turtle by Controlling Instinct Behavior via Human Brain-computer Interface," Journal of Bionic Engineering, vol. 13, No. 3, XP029642640, Jul. 2016, 14 Pages.

Hengameh Marzbani, et al., "Methodological Note: Neurofeedback: A Comprehensive Review on System Design, Methodology and Clinical Applications," Basic and Clinical Neuroscience Journal, vol. 7, No. 2,XP055433279, Apr. 2016, pp. 143-158.

Lisa Maria Glenk, "Current Perspectives on Therapy Dog Welfare in Animal-Assisted Interventions," Animals, vol. 7, No. 7, 2017, 17 Pages.

Eduardo Kac, "Telepresence artwork," Retrieved from the Internet [URL: http://www.ekac.org/darker.html], 1999, 2 Pages.

* cited by examiner

SYSTEM AND METHOD FOR NEUROFEEDBACK TRAINING THAT UTILIZES ANIMAL IN THE FEEDBACK LOOP

FIELD OF THE INVENTION

The present disclosure is directed to a new system and method for neurofeedback (NFB). Accordingly, embodiments of the disclosed subject matter can be classified as a diagnostic device that detects, measures or records bioelectric signals of the body or a part thereof; namely bioelectrical signals produced by brain's activity. In principle that is the field of electroencephalography (EEG) in the sense that EEG signals are used to create neurological biofeedback, also known as neurofeedback.

Neurofeedback, further in the text denoted as NFB, represents a noninvasive method that is used to gradually improve brain's functions. With NFB or EEG feedback, brain activity is measured and fed back in real time, and due to that, over the course of time, brain's self-regulation is achieved and neurological disbalance is decreased and/or annulled. Neurological disbalance may be the result of different brain function deteriorating processes. NFB, thanks to brain's plasticity, increases quality of the brain's neural network, which, as the result, makes the NFB trained brain to work better.

NFB principle of operation is relatively simple; a set of EEG electrodes is placed on a subject's scalp, following a protocol that is determined by symptoms of the subject. Brainwaves are detected by means of EEG electrodes and processed on a computer in real time. EEG electrodes do not inject current and no harm can be done by using them. It is worth to note that NFB setup, due to smaller number of EEG measuring electrodes, cannot be the substitute for a "clinical EEG" that is used for medical diagnostics. In order to present to the subject a feedback about their brain functioning during NFB training, brainwaves and other information obtained in the process are processed by the computer. The feedback can be presented to the subject in different ways; usually as variations in the playback of audio-visual recording or actions in videogames.

After a sufficient number of training cycles, the subject's brain starts to produce "desired" brainwaves and suppress "undesired" ones, that is the very goal of NFB. In many cases NFB has positive and permanent effect, yet in some cases training cycles have to be repeated indefinitely. Small percentage of cases display no changes due to NFB, and it is impossible to predict with absolute certainty to what extent NFB would be useful in an isolated case.

Technical Problem

Due to the use of BEG electrodes plugged into electronic device that is further connected to a computer in order to process said received EEG signals into video, audio or tactile feedback signal for a subject, it is very difficult to conduct NFB in a natural environment. Furthermore, NFB systems are difficult to move or use outdoors, due to poor visibility of screen content in daylight.

But, by far the greatest obstacle to performing NFB in natural environment is the fact that, when in nature, brain processes a lot of visual information making it difficult for a subject to maintain focus on the computer screen. This essential technical problem is solved by embodiments of the disclosed subject matter by modification of the standard NFB chain:

subject-EEG signals-processing-screen-user in a way that instead of the screen trained animal is used:
subject-EEG signals-processing-trained animal-user In other words, NFB is implemented in a way that, after the signal processing and algorithmic decisioning is finished, the data processing system sends a command to the animal which the subject is looking at. Since the animal is a natural part of the natural environment it is easy for the subject to keep the focus on her. The main advantage of this approach is that such modified. NFB can easily be conducted in a natural environment; e.g. park, meadow, large swimming pools.

Bearing in mind that the system has to communicate with the animal, without distraction and subject's knowledge, the second technical problem is revealed, i.e. how to perform such communication in a simple and practical manner. According to the said invention, the best way is to use trainable animals that communicate naturally with sounds of frequency that is above human hearing range; i.e. in frequencies above 20 kHz. The first selections are certainly sea mammals: dolphins and whales. The dogs are also suitable selection because, even if they communicate with humans in "normal" frequency range, they are susceptible to sounds with frequency higher than 20 kHz.

The third technical problem refers to multiple NEB trainings performed simultaneously in the same place; i.e. when more than one person and more than one animal are in the same space, where by the word "space" we define an area in which the interferences between ultrasonic communications are possible. This technical problem is solved by training animals to react only to ultrasonic signals of specific shape, i.e. wave train. In other words, each animal included in a NFB has own set of the sound codes and is trained to ignore commands with other wave trains, i.e. codes. A good example to said is when a horse ignores a gunfire, because that signal has no meaning to the horse.

Previous State of the Art

Prior art is rich in both patent and non-patent literature.

International patent application published as WO2016/139576A2 for the invention: "BRAIN ACTIVITY MEASUREMENT AND FEEDBACK SYSTEM", filed in the name of Mindmaze S. A., Switzerland; teaches of many NBF variations wherein the main feature is a user module (headset) with micro-screens for projecting of the NFB content. This system can overcome physical barriers of a conventional NFB system, yet it remains opened. question how the "closing" of the visual field affects the NFB performance. Furthermore, the document does not include the use of animals in any way. This patent application represents a document defining the general state of art, which is not considered to be of particular relevance.

International patent application published as WO2015/035058A1, for the invention: "SYSTEM AND METHOD FOR ANIMAL HUMAN NEURAL INTERFACE", filed in in the name of Northwestern University, USA; teaches of a direct human to animal electrical neural link. The described system is invasive to the animal and/or human as seen from claims 1 and 3 of the document; there is a need to implant electrodes in body parts of the animal and human. It must be noted that most human-animal interfaces are implemented in an invasive way; which, inter alia, is not ethically allowed and leaves physical and psychological trauma to all chain participants. This patent application represents a document defining the general state of art, which is not considered to be of particular relevance.

International patent application published as WO2009/102345A1, for the invention: "MOBILE DEVICE DOG WHISTLE", filed in the name of Sony-Ericsson Mobile Communication AB, Sweden; teaches of a technical solution where a mobile device is transformed into ultrasonic emitter which communicates with animal in the performance area by means of ultrasound. Communication to the animal is performed for the purpose of defense or the animal training. This invention is relevant due to the fact that it discloses a connection of an animal and a mobile device. The significant difference in comparison with embodiments of the present disclosure is the absence of a feedback between the animal's action and subject's EEG pattern; although in the part of the chain a trained animal that is susceptible to ultrasonic signals is used. Thus, the cited patent application represents a document defining the general state of art, which is not considered to be of particular relevance.

Chinese patent application CN104049979A for the invention "UNIVERSAL ULTRASONIC DOG TRAINING DEVICE AND DOG TRAINING METHOD", filed in the name of Shanghai Feixun Comm. Co. LIM, Kina; teaches about the device for training, and subsequent control, of an animal that is independent of the speech of the person communicating with the animal and the corresponding use of the said device. According to the abstract, the device consists of a command-to-ultrasonic signal translation module, an ultrasonic animal training module, an information storing and a control and ultrasound emission module. This document is relevant due to the fact that embodiments of the present disclosure can also use the animal training module in order to provide an adequate, previously entrained, animal reaction to a given EEG pattern. It is worthy to note that the cited document remains silent about the use of EEG signals nor the connection human-animal-human as a part of NEB chain. Thus, this patent application represents a document defining the general state of art, which is not considered to be of particular relevance.

The article L. M. Glenk: "CURRENT PERSPECTIVES ON THERAPY DOG WELFARE IN ANIMAL-ASSISTED INTERVENTIONS"; Animals 2017, 7(2), 7 doi:10.3390/ani7020007 available at: mdpi.com teaches about the aspects of using a dog in a so called AAI (Animal Assisted Interventions). Within the AAI animals are used as a support for human health improvement therapies. The article discusses, using exact parameters, the practice use of dogs in the therapeutic environment, considering the aspect of the AAI effect on animals, which has not been analyzed before. The relevance of this document is the fact that it discusses the use of trained animals for AAI, which may re considered a significant element of embodiments of the present disclosure; although, the document does not teach about the use of animals as a part of NEB chain. Therefore, this document represents a document defining the general state of art, which is not considered to be of particular relevance.

The document "TELEPRESENCE ARTWORK" of e author E. Kac, Slovenia; represents an attempt to understand behavior of bats by visualizing ultrasonic communication of other bets in an artificial cave, by the use of an artificial bat as a sensor and a virtual reality user module; as seen at the link: ekac.org. The document reveals the aspect of the following chain: bat-hardware-human, but the document remains silent regarding the feedback loop disclosed. by embodiments of the present disclosure. Therefore, this document represents a document defining the general state of art, which is not considered to be of particular relevance.

The article of group authors; Cheol-Hu Kim, Bongjae Choi, Dae-Gun Kim, Serin Lee, Sungho Jo, Phill-Seung Lee: "REMOTE NAVIGATION OF TURTLE BY CONTROLLING, INSTINCT BEHAVIOR VIA HUMAN BRAIN-COMPUTER INTERFACE"; Journal of Bionic Engineering, 2016; 13 (3): 491 DOI: 10.1016/S1672-6529 (16)60322-0; that can De found at: researchgate.net tea les of turtle's motion controlled by a human via human turtle connection performed with the EEG based Brain-Computer Interface. The turtle is stimulated for certain motion the use of her instinct to find the light, namely, a special device placed on the turtle's head covers parts of vision field according to human's EEG signals. This document is relevant because it shows noninvasive implementation of some elements of feedback loop human-animal-human. It is essential to note that the NFB, per se, induces measurable changes in the subject's EEG pattern and in the cited"turtle control system" the subject's EEG pattern has not been changed in a therapeutic manner. Namely, a human observes a position of a remote animal via camera placed on the animal, and by his will (e.g. visualization of movement) produces certain EEG pattern that, after being recognized and processed by EEG analytics, changes turtle's vision field which causes the turtle to move in desired direction.

Differences between cited document and embodiments of the present disclosure are in the use of a trained animal—which a turtle, surely, cannot be—and in the change of the subject's EEG pattern, which is the result of the therapeutic effect of NFB. Namely, embodiments of the present disclosure can comprise a module by which the animal's behavior affects humans' EEG pattern and in the cited document the effect is exclusively from human to animal without the feedback's benefit.

SUMMARY

Embodiments of the present disclosure can discover a method of operating a system for neurofeedback (NFB) training on a subject that includes trained animal species in a feedback chain. The described system can be comprised or consist of at least one user module, mobile module, and option modules. Option modules can be selected from, so called, separated modules that are placed in the NFB performance area and an animal module that is placed on the animal.

The user module can be equipped with EEG electrodes for brainwave recording, an EEG amplifier, an EEG signal processing unit that converts EEG signals to digital recordings suitable for wireless transfer, a pairing unit to enable connectivity with other modules and an ultrasonic speaker for communication with the trained animal. Mobile module can be equipped with data processing unit that processes EEG signals of one or more users and a pairing unit to enable connectivity with other modules. Also, mobile module can comprise additional animal training modules, control module, and internet module for data cloud connectivity. All these modules can be connected with the data processing unit. Both option units can be equipped with: a data processing unit, a pairing unit to enable connectivity with other modules and ultrasonic speaker for communication with animals.

The therapeutic NFB on the subject can be performed by means of the system which performs a closed chain of steps below:

A→B→C→D→A wherein:
A. represents real time recording of the subject's EEG performed by the user module and forwarded to the mobile module by using their respective paired units;
B. analytics of the signal recorded in the step A. performed by the data processing unit of the mobile module, and algorithmic decisioning about the stimulation form for the subject whose EEG signal has been recorded;
C. forwarding the stimulation form for the subject determined in the step B. towards the animal by using one or more ultrasonic speakers simultaneously, placed on the user module, on the separated module and/or animal module; wherein all the mentioned modules are paired with the mobile module; and wherein the information needed for the animal performance is forwarded in the form of a coded ultrasonic signal; and
D. performing of a learned action by the animal triggered by the received ultrasonic signal from the step C. which provides a stimulus to the subject exposed to the neurofeedback training of the step A.

Suitable animal species for the use in NFB training are dogs and dolphins. In one embodiment, the mobile module is wearable and placed on the subject, separated or as a part of the user module, while changes, control and interventions are made via internet connection with data cloud. Pairing units of the above cited modules use short-range communication means.

In one embodiment, for communication in the step C. ultrasonic speaker is placed only in the user module. In another embodiment the ultrasonic speaker that is placed in the animal module which is noninvasively mounted on the animal in the form of a patch or a collar. In yet another embodiment, in the step C., the ultrasonic speaker is integrated in the separated module which is placed in the performance area.

In yet another aspect of embodiments of the present disclosure, the connection mobile module—option modules, i.e. respective ultrasonic speakers, is used for the training of the selected animals.

In yet another aspect of embodiments of the disclosure, one or more mobile modules process information from the step A. for multiple users in order to control multiple animals in a way that each animal has been trained for a different set of ultrasonic commands. Thus, multiple independent NFB therapies can be performed without interference.

Embodiments of the present disclosure also involve a communication system for performing neurofeedback at subjects that include other trained animal species in the NFB chain in a way that it comprises means for conduction of previously stated procedures. The described system, being the simplest one, according to one or more embodiments, can be the one where:
  the user module and mobile module comprise one module without the control unit,
  the control of the module is implemented in a way that it is performed exclusively by means of the data cloud, and
  that new module can be paired with any option module in order to improve NFB performance.

DETAILED DESCRIPTION

As already mentioned in previous sections, a NFB is a noninvasive method that improves brain functioning when used over a period of time. Historically, it dates back in 1924 when psychiatrist Hans Berger connected, by means of noninvasive electrodes, patients scalp to a galvanometer and made the first recording of brainwaves. Development of measurement methods and improved hardware enabled discoveries and subsequent classification of brainwaves according to their frequency ranges; see FIG. 5. Today we distinguish the following waves: delta waves from 0.2-3 Hz, theta waves from 3-8 Hz, alpha waves from 8-12 Hz, beta waves from 12-27 Hz and gamma waves from 27-100 Hz.

In the last decade NFB is being used for treatments ranging from ADHD to alcoholism. More information can be found in the review: D. Corydon Hammond, PhD, ABEN, QEEG-D "An Introduction to Neurofeedback"; available at: appliedneuroscience.org.au.

Figure 1:
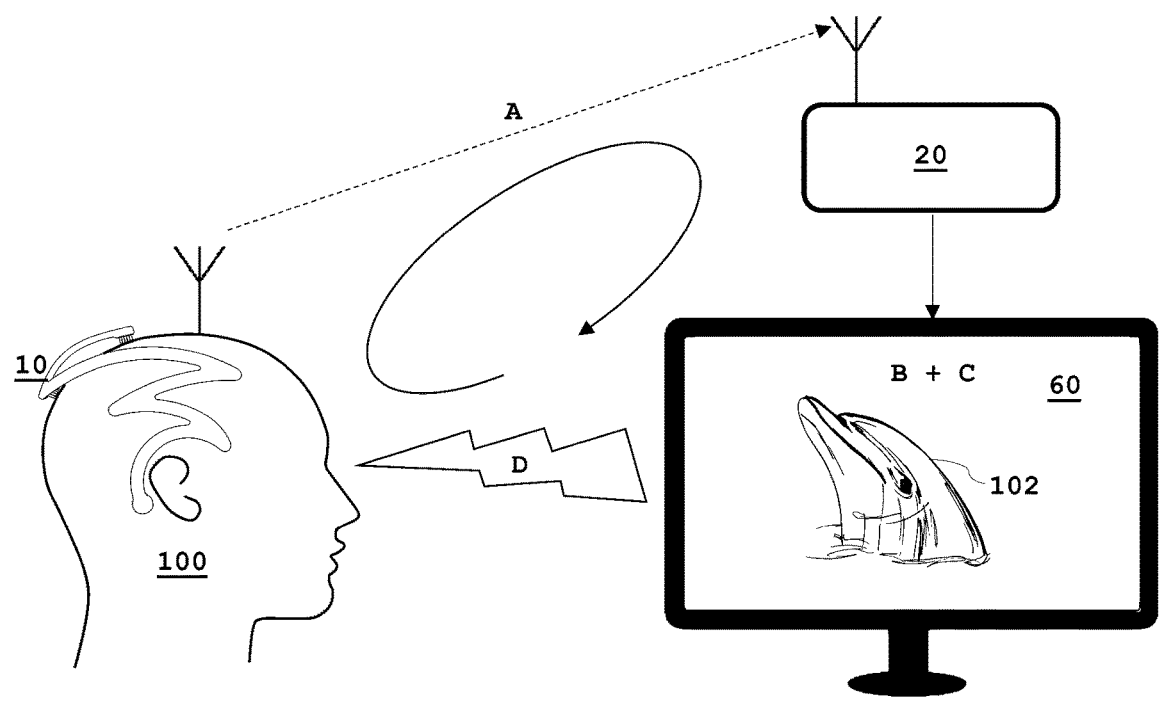
FIG. 1 represents prior art regarding NFB stimuli is a display on which the content subject's EEG patterns is displayed.

Traditionally, NFB is conducted as shown in FIG. 1: the treated subject (100) has on his head the user module (10) equipped with electrodes (11). The user module (10) is connected, usually by wire and since recently wirelessly, with the mobile module (20). The purpose of the user module (10) is to ensure reliable acquisition of the subject's EEG activity and transfer it to the mobile module (20) for further processing. The mobile module (20) or it's technical equivalent—stationary device (20)—processes received signals and, according to the preprogrammed scenario, displays, on the computer screen (60), images, video, and produces sound or some other stimulus, e.g. tactile—that the subject (100) can perceive. Neurological activity induced in the process changes the subject's (100) EEG patterns in a desired way. This is the traditional, i.e. standard, way to make the NFB communication loop closed; step A in FIG. 1 represents forwarding of the EEG recordings to the module (20), step B represents analytics of the received EEG signal, step C represents a generation of the stimulus according to the analytics performed in step B, while step D is a transfer of formed stimulus to the subject (100).

Figure 2:
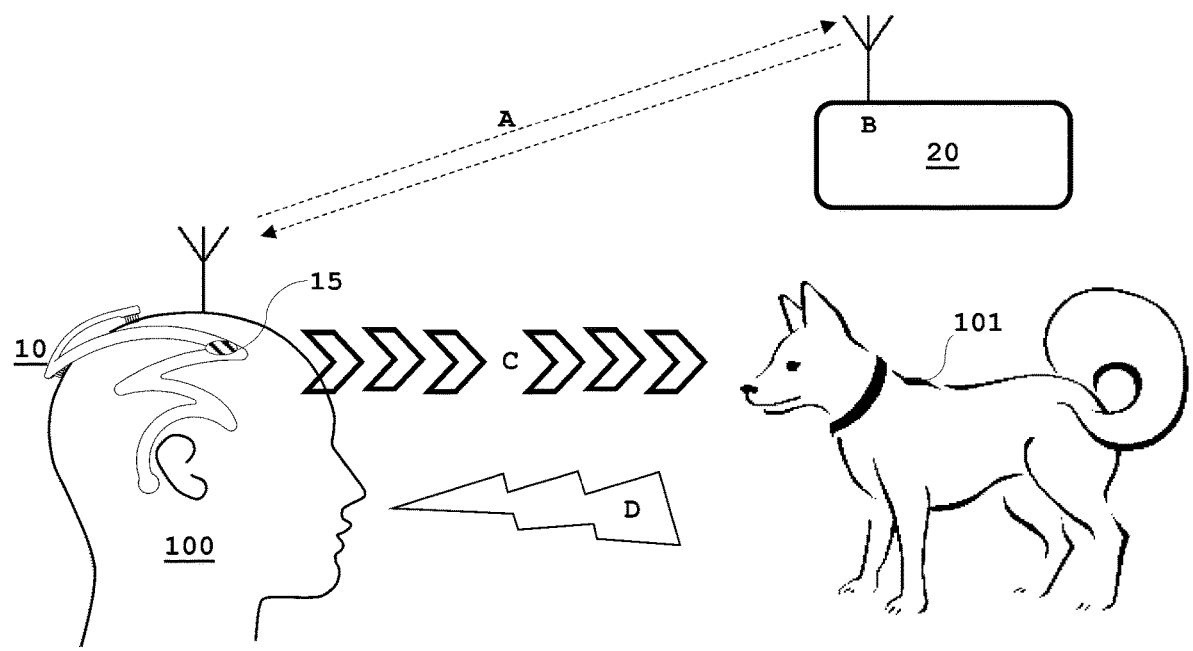
FIG. 2 represents NFB setup according to embodiments of the disclosed subject matter, in which other animal species are used in the feedback chain; letters A, B, C and D denote steps explained in the previous section.
Figure 3:
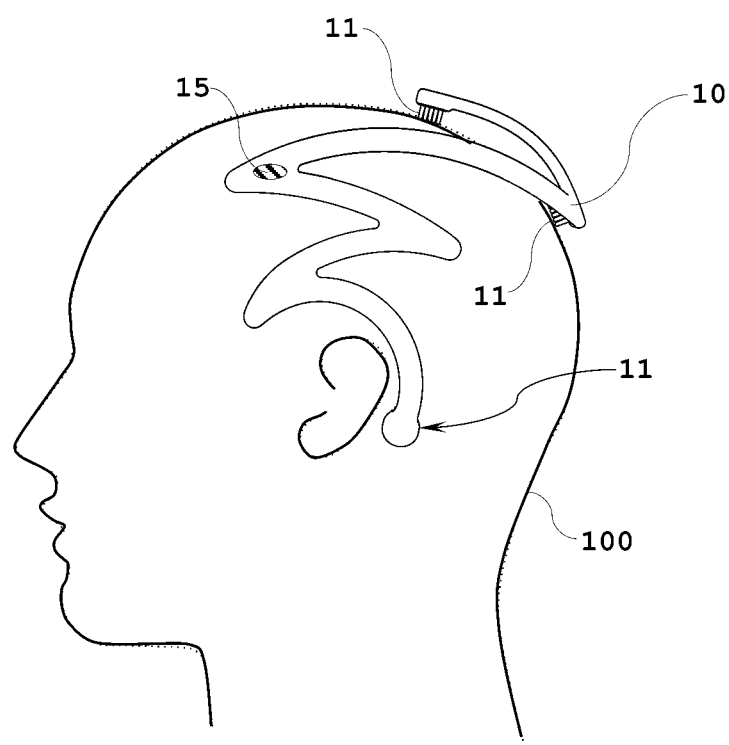
FIG. 3 represents one version of the wearable user module.
Figure 4:
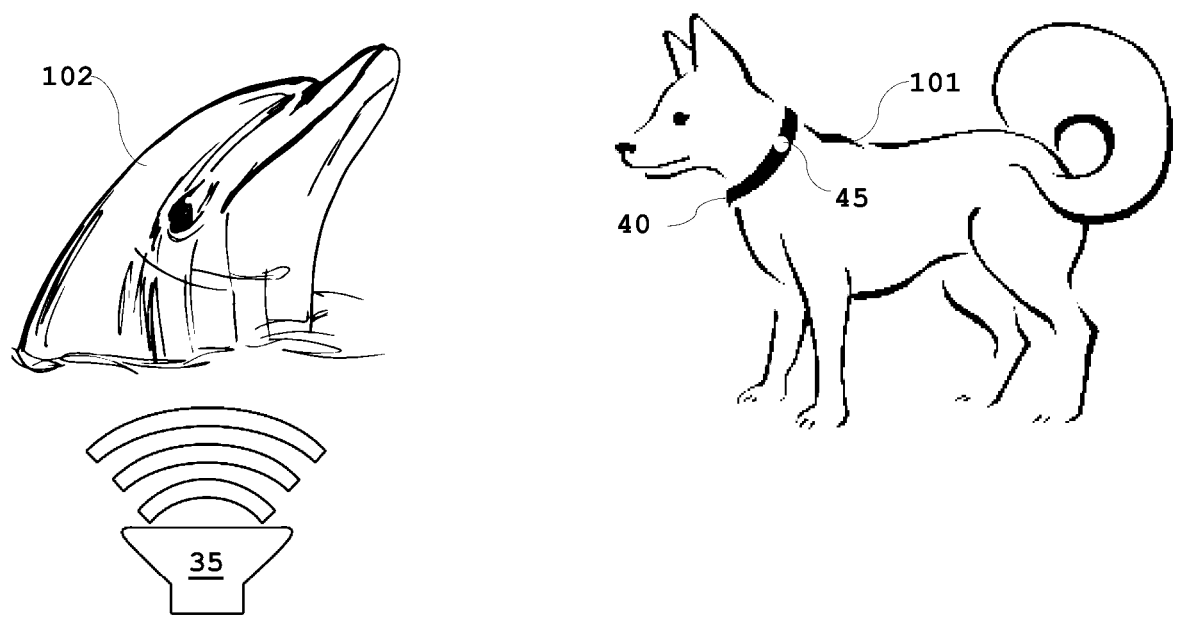
FIG. 4 represents the animals controlled by ultrasound via using, so called, a separated module and the module attached to an animal.

A main difference between the embodiments of the disclosed subject matter and the traditional NFB can be the fact that one element of the feedback loop is a trained animal (101, 102); susceptible to ultrasonic stimuli. The difference can clearly be seen in FIG. 2; the user module (10) is equipped with EEG electrodes (11) placed on the scalp, where one of possible configurations is shown in FIG. 3. The user module (10) is connected, usually by wire and since recently wirelessly, with the mobile module (20). The mobile module (20) or his technical equivalent—stationary device (20)—processes received signals and, according to the preprogrammed scenario in one or more embodiments of the disclosed subject matter, returns information about the stimulation or activation of the animal to the user module (10). The user module (10) activates ultrasonic speaker (15) and directs ultrasonic command to the previously trained animal (101, 102), e.g. dog. On the basis of the received ultrasonic command, the dog performs "a trick" that is visual, e.g. chases his own tail; or tactile, e.g. approaches to the subject (100) and cuddles; or auditory—barks. Such behavior of the animal (101, 102) is used for the NFB and produces changes in the subject's (100) EEG signal that is acquired by means of electrodes (11). Such signal is subsequently used to produce the next signal in the user module (10). In this way the NFB loop is completely closed, according to embodiments of the disclosed subject matter.

There are numerous advantages of this kind of NFB's implementation; the NFB in not limited to the closed performance arena, the produced live animal feedback can have significant impact on the subject's EEG that is more intensive when compared with the feedback produced by watching images on the screen (60) as is the case in traditional NFB implementation. One drawback may be that NFB implementation according to embodiments of the present disclosure can require trained animal (101, 102). Especially suitable species susceptible to ultrasonic commands are canines, i.e. dogs; as well as dolphins and whales that communicate in the ultrasonic range also. For other suitable animal species details can be found here: en.wikipedia.org.

In case that performance area is a large open space it can be useful to use additional modules for generation of ultrasonic signals; e.g. underwater modules for dolphins/whales or external modules in large parks for dogs. Each additional module can be separated standalone module (30), or an animal module (40) that is noninvasively placed on the trained animal (101, 102). It can be formed as a dog collar; or a sticky patch for dolphins or whales. It is worth to note that mentioned modules should not prevent animals in their natural behavior within given environment. The number of these option modules is arbitrary.

As already mentioned, NFB implementation according to embodiments of the present disclosure can use trained animal in the feedback loop. The prior art document CN104049979 teaches about one way to train for NFB. As mentioned before, the response to ultrasonic commands must be fully individualized; i.e. each animal should have its own set of coded commands which in turn enables simultaneous conduction of NFB of many subjects (10) in the same performance area.

Figure 5:
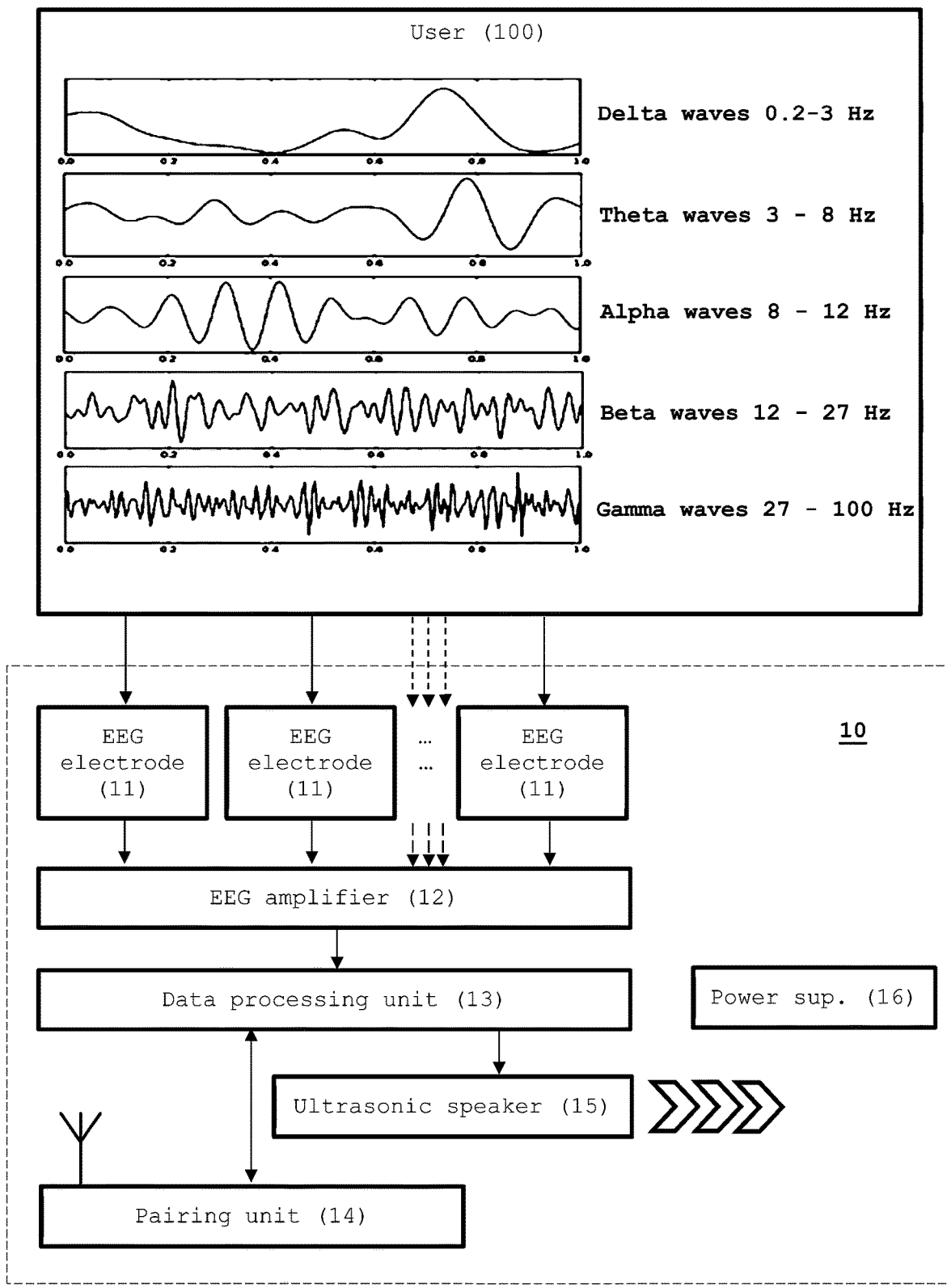
FIG. 5 represents different types of brainwaves that are sampled by the user module and the hardware integrated in the user module.

FIG. 5 shows in detail one possible construction of the user module (10). It has helmet-like shape and size such that it can be put on the head so that EEG electrodes (11) fit well on the subject's (100) head and touch the subject's (100) skin in a way that the subject's (100) brainwaves can be recorded. The signal from one or more EEG electrodes (11), usually less than 100 µV, is led to an EEG amplifier (12) in order to be processed by data processing unit (13). The data processing unit (13) converts that signal to digital record by means of analog-to-digital converter; or, even better, convert it to pulse-width-modulated wireless signal. Such system, specially adapted for energy efficient transmission of EEG signals, is disclosed in the European patent EP3005570B1 with the title "ENERGY-EFFICIENT SYSTEM FOR DISTANT MEASUREMENT OF ANALOGUE SIGNALS"; filed in the name of Sveuciliste u Osijeku, Fakultet elektrotehnike, . . . .

Once digitalized, or analogously modulated, EEG signal can be, by means of the pairing unit (14), transferred to the mobile unit (20), i.e. it's pairing unit (25). Examples of good pairing means are: asynchronous UWB (ultra wide band) communication, any communication protocol used for IoT (Internet of Things) or well-known Bluetooth® modules. The main problem of the present communication is energy efficiency that reflects to the power supply (16) autonomy, without which the user module (10) becomes useless. It should be noted that it is favorable that all the pairing units (14) use duplex communication; which is not a necessary condition but certainly an advanced design.

Figure 6:
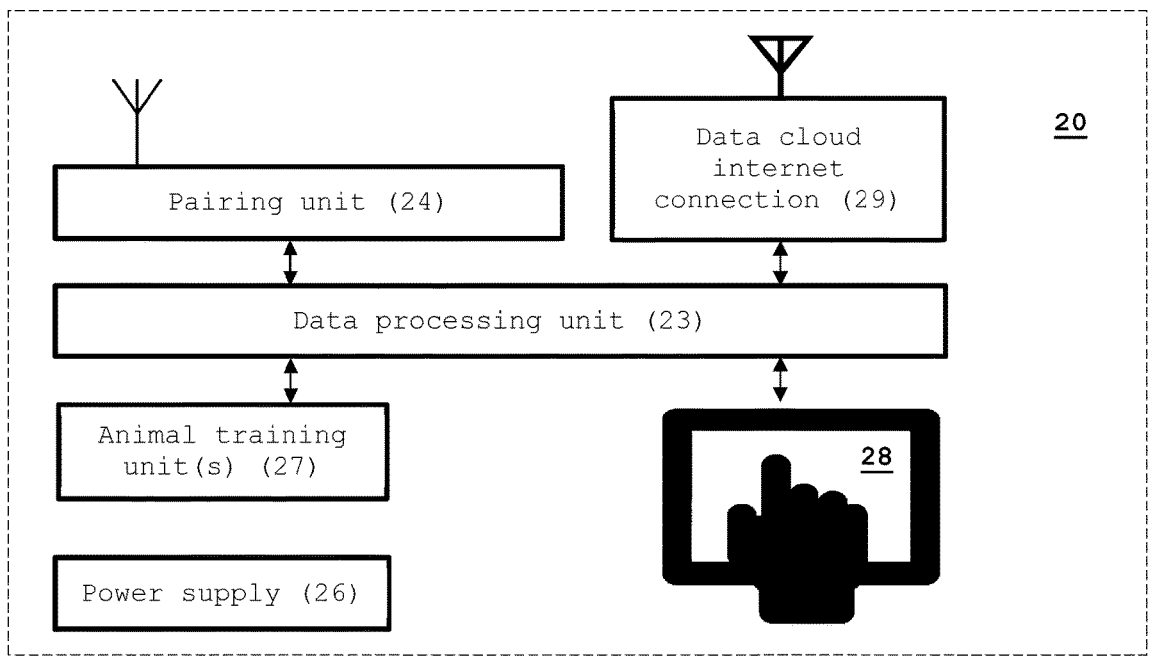
FIG. 6 represents a diagram of mobile module hardware.

FIG. 6 shows one embodiment of the mobile module (20) or it's stationary technical equivalent. The term "mobile" relates to the fact that it is the size of a mobile ultra-book, with work autonomy of about 10 hours, and is used by a therapist/technician to perform or supervise the NFB for example in nature, where the animal (101, 102), e.g. the dog, that is a part of the feedback loop, is located. That mobile module (20) is in one embodiment a modified ultrabook or a smartphone, that is at the same time the data processing unit (23), while the pairing unit (24) depends on the choice of the user module (10). Namely, if the user module (10) uses Bluetooth® for communication with the mobile module (20), then the pairing unit (24) is a part of the data processing unit (23). Data processing unit (23) comprises or can access animal modules (27) that are usually composed of programming code and instructions for animal training. Mobile module (20) can be connected to the data cloud (50) via standard internet connection (29). In practice, additional parallel analysis can be made in the data cloud (50); each NFB subject (100) can be monitored and the CRM (customer relation management) can be provided. Mobile module (20) is equipped with the control unit (28) that can be implemented as a touch screen, by means of which the person supervising NFB can influence the behavior of the animal (101, 102) regardless of the performed analytics on the subject's (100) EEG pattern. The power supply (26) is usually integrated with the data processing unit (23) that is a solution which is common in the art.

Figures 7, 8:
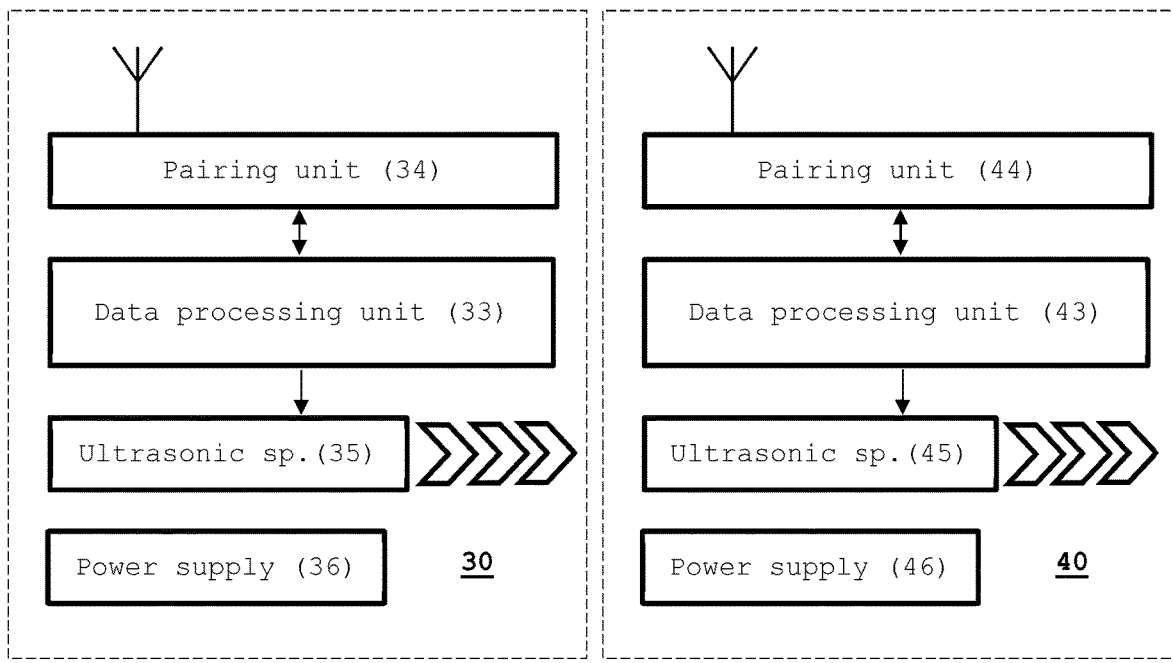
FIG. 7 and FIG. 8 represent the diagram of the separated module and the animal module, respectively.

FIGS. 7 and 8 show the embodiment of the optional modules that can be implemented as the standalone separated module (30), or the animal module (40). Both modules are built similarly, animal module (40) being smaller and fit for mounting on the animal (101, 102). Each of the mentioned optional modules (30, 40) contains the pairing unit (34, 44) by which it can be paired with the mobile module (20) and/or the user module (10) according to the configuration chosen by the NFB operator. Data processing unit (33, 43) translates received instruction to the ultrasonic signal that is subsequently emitted by the ultrasonic speaker (35, 45) to the chosen animal (101, 102). Power supplies (36, 46) ensure the anatomy of the mentioned devices for a period of couple of hours.

Some of possible embodiments are shown in FIG. 9-12.

Figure 9:
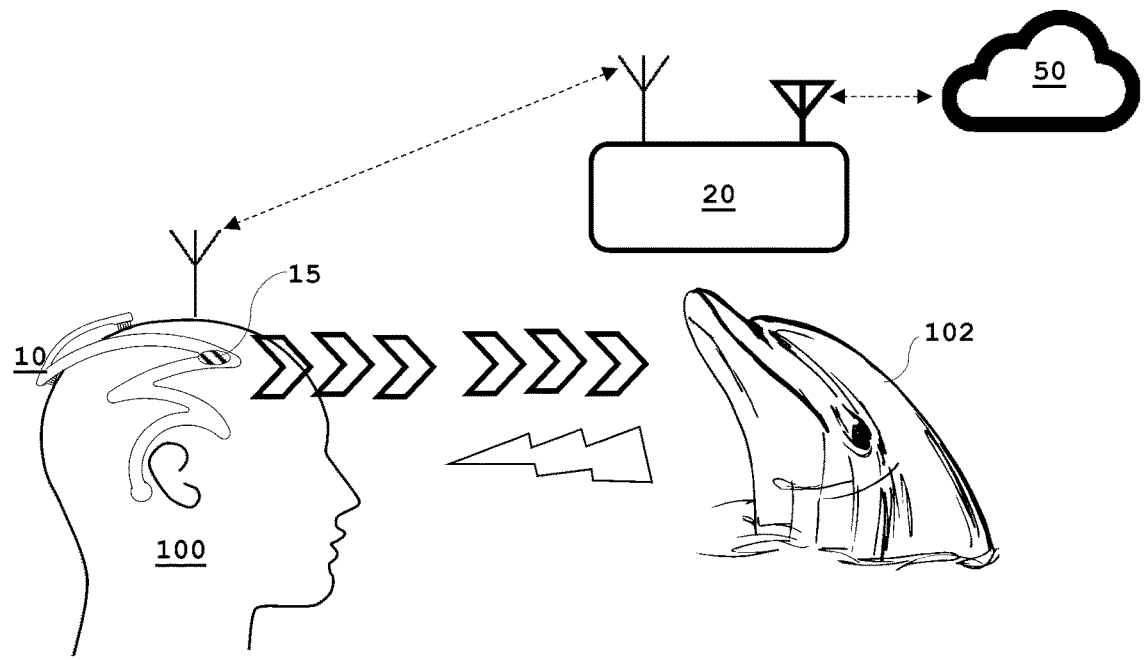
FIG. 9 represents NFB implemented through the use of user module and mobile module.

FIG. 9 shows the basic configuration where NFB is performed in 4 steps closed into a loop, as shown below:

$$A \rightarrow B \rightarrow C \rightarrow D \rightarrow A$$

where:
A. represents real time recording of the subject's (100) EEG performed by the user module (10) and forwarded to the mobile module (20) by using their respective paired units (14, 24);
B. analytics of the signal recorded in the step A., performed by the data processing unit of the mobile module (23), and algorithmic decisioning about the stimulation form for the subject (100) whose EEG signal has been recorded;
C. forwarding the stimulation form for the subject (100) determined in the step B. towards the animal (101, 102) includes, according to this embodiment, forwarding of instructions of stimulation to the paired user module (10) that performs activation of its ultrasonic speaker (15) by which the required information is emitted to the animal (101, 102) in the form of coded ultrasonic signal; and
D. performing of a learned action by the animal (101, 102) triggered by the received ultrasonic signal from the step C. which provides a stimulus to the subject (100) exposed to the neurofeedback training of the step A.

Step D→A closes the loop of the said NFB.

Figure 10:
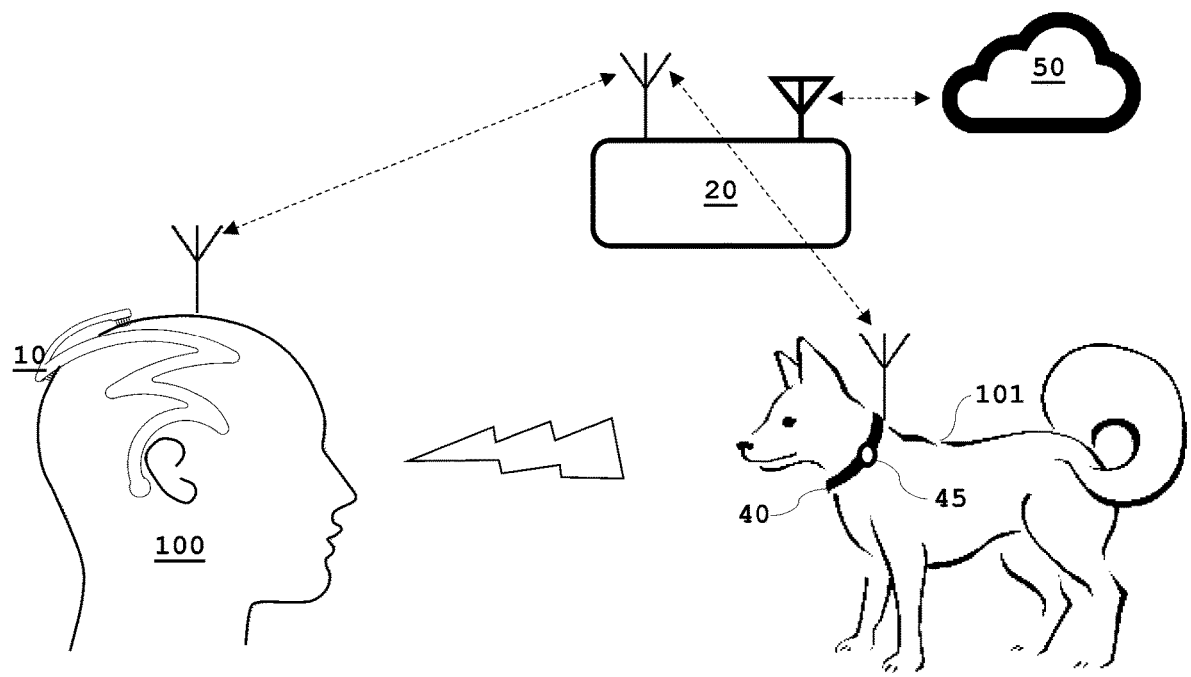
FIG. 10 represents NFB implemented by the use of user module, mobile module and the module that is placed on the trained animal.

In yet another embodiment according to the present disclosure shown in FIG. 10, in the step C. signal travels directly to the paired optional animal module (40) that uses ultrasonic speaker (45) in order to transfer the needed information to the animal (101, 102). In this embodiment, a consistent connection to animal is established, regardless of the distance between the animal and the subject (100) or the mobile module (20).

Figure 11:
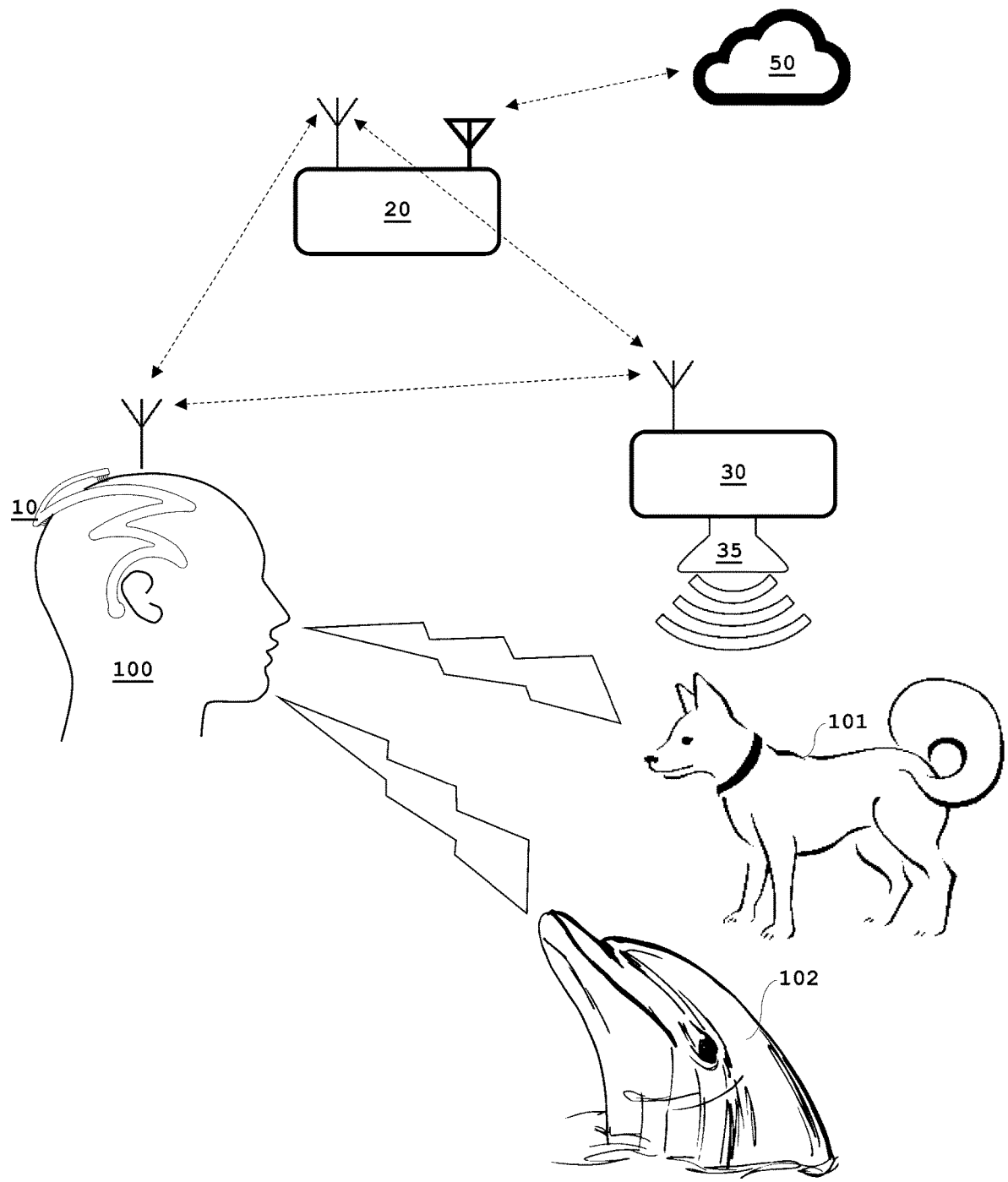
FIG. 11 represents NFB performed by means of user module, mobile module and separated module.

In yet another embodiment according to the present disclosure shown in FIG. 11, in the step C. the signal travels directly to the paired separated module (30) which uses its ultrasonic speaker (35) to transfer the needed information to the animal. In this embodiment, a consistent connection to the animal is again established. In case when the medium is water and the animal is dolphin (102), the preferred position of the ultrasonic speaker (35) is a submerged position.

Figure 12:
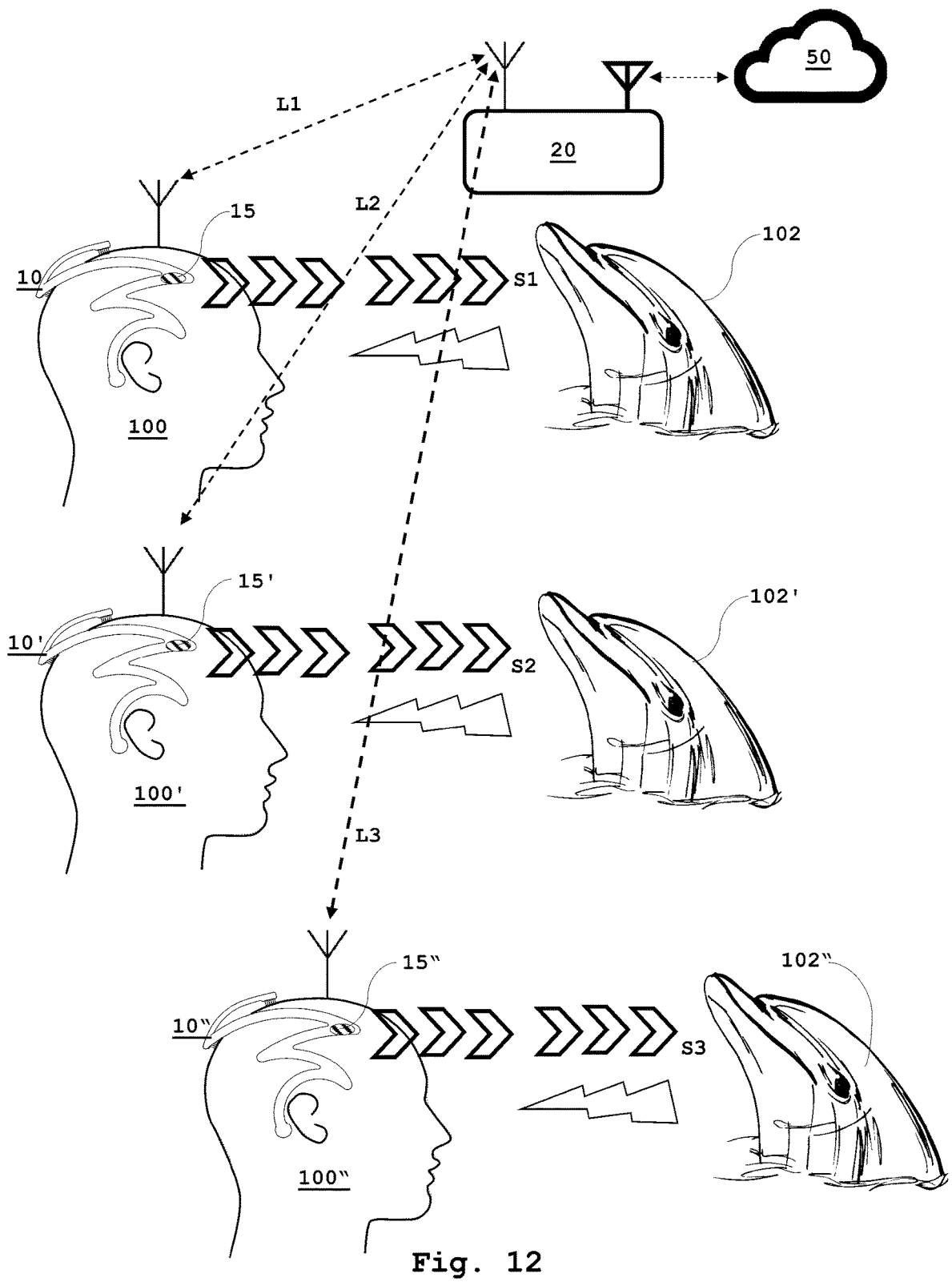
FIG. 12 shows multiple NFBs realized between subject-animal pairs wherein all the control is performed by a single mobile module.

FIG. 12. shows example of multiuser interface connected to one mobile module (20). The situation for each subject (100, 100', 100'', . . . ) is identical to the one previously described for FIG. 9. Yet, in this case one mobile module (20) is connected via link (L1, L2, L3, . . . ) by the use of the pairing unit (24) with the series of pairing units (14, 14', 14'', . . . ) placed within user modules (10, 10', 10'', . . . ). Each independent user module (10, 10', 10'', . . . ) controls one ultrasonic signal (S1, S2, S3, . . . ) emitted from the ultrasonic speaker (15, 15', 15'', . . . ) in order to control the animal (102, 102', 102'', . . . ) of one of NFB, NFB', NFB'', . . . . Namely, one mobile module (20) has sufficient processor power to serve almost any given number of user modules. This configuration is very convenient when there are more subjects in the same NFB performance area.

Figure 13:
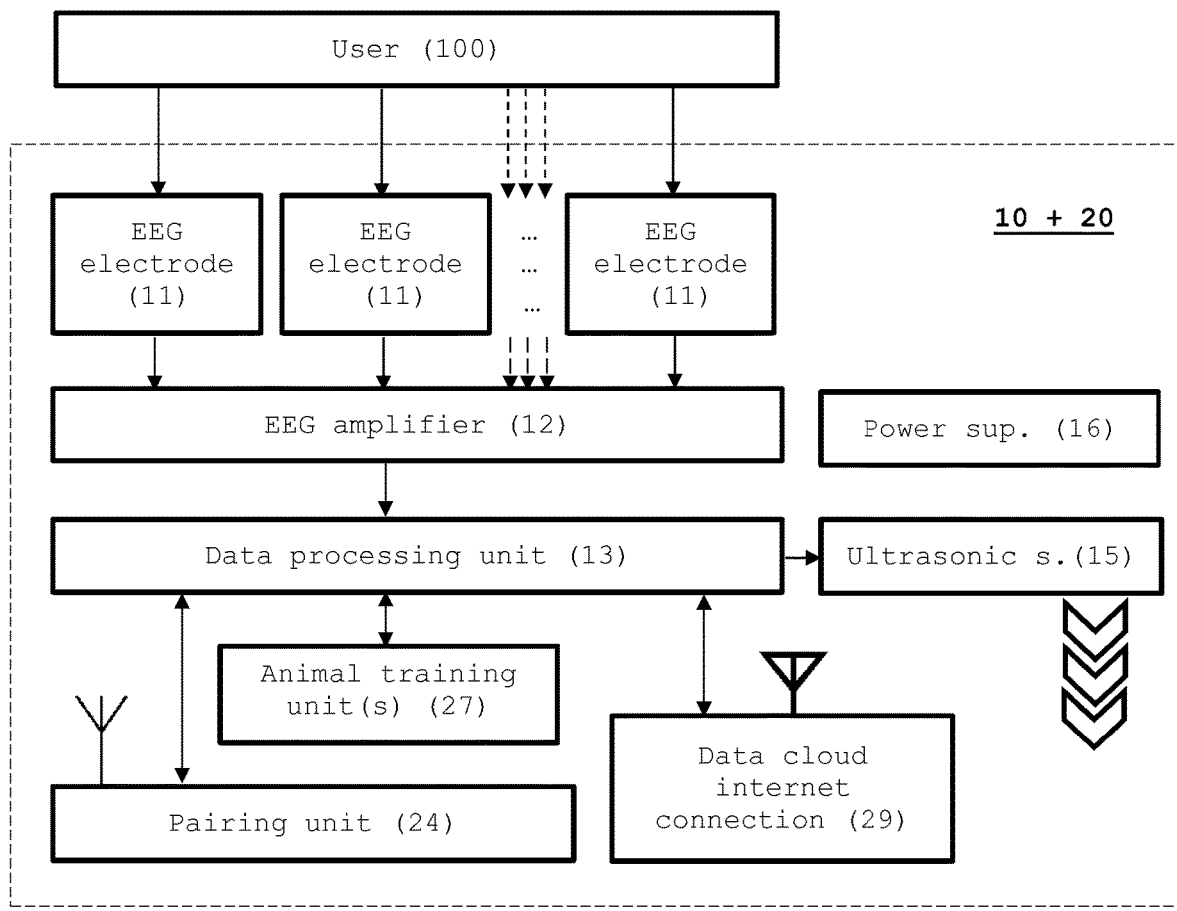
FIG. 13 shows one variant of the invention where the user module and the mobile module are integrated in a single module.
Figure 14:
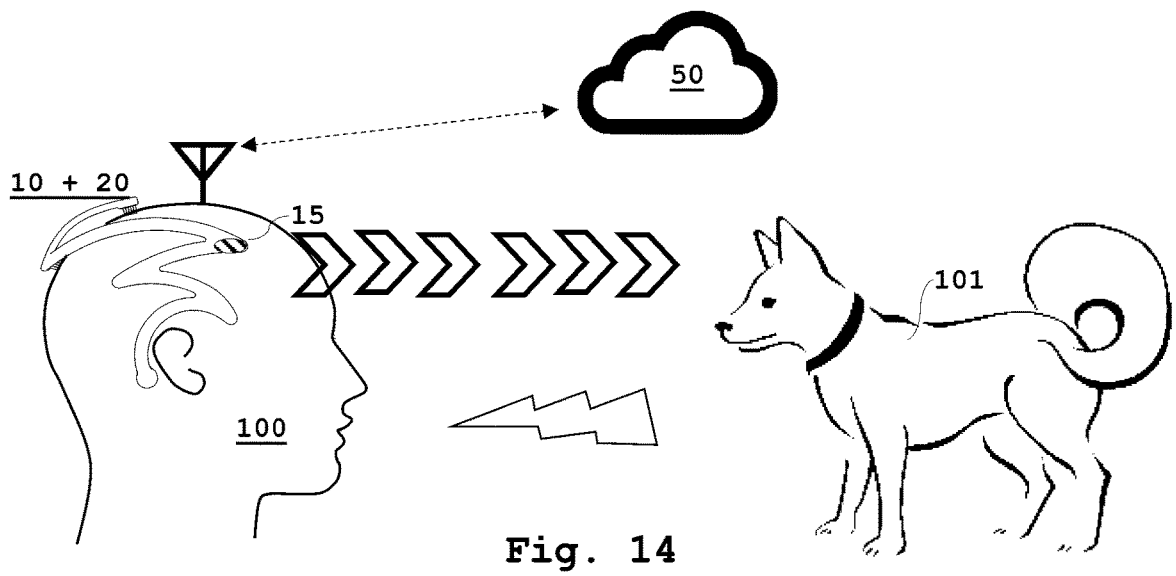
FIG. 14 represents the use of such all-in-one module for NFB.

In yet another embodiment according to the present disclosure, the mobile module (20) and the user module (10) are integrated into one module; see FIG. 13. In this integrated module the data processing is performed and animal module (27) as well as the data cloud internet connection (29) is also added. The mentioned internet connection to the data cloud is used for control of such an integrated module. In this case NFB looks as shown in FIG. 14, yet different ways of pairing with optional modules (30, 40) are possible as well as pairing with other user modules (10', 10'', . . . ) which is obvious to an average person skilled in the art. The number of possible combinations according to the invention are sufficiently large enough that any operator/supervisor can choose the optimal way to perform NFB on a subject (100).

INDUSTRIAL APPLICABILITY

The industrial applicability of embodiments of the present disclosure is obvious, whereby the discovery of a method of implementation of NFB on the subject (100) that includes other trained animal species (101, 102) in the feedback chain, as well as the system for neurofeedback (NFB) training itself.

REFERENCES

- 10 User module
- 11 EEG electrode
- 12 EEG amplifier
- 13 Data processing unit
- 14 Pairing unit
- 15 Ultrasonic speaker
- 16 Power supply
- 20 Mobile module
- 23 Data processing unit
- 24 Pairing unit
- 26 Power supply
- 27 Animal training unit
- 28 Control unit
- 29 Data cloud internet connection
- 30 Separated module
- 33 Data processing unit
- 34 Pairing unit
- 35 Ultrasonic speaker
- 36 Power supply
- 40 Animal module
- 43 Data processing unit
- 44 Pairing unit
- 45 Ultrasonic speaker
- 46 Power supply
- 50 Data cloud
- 60 Screen
- 100 Subject
- 101 Dog
- 102 Dolphin
- S Ultrasonic signal
- L Established link

The invention claimed is:

1. A method of operating a system for neurofeedback (NFB) training on a subject that includes an animal species in a feedback chain, the system comprising at least one user module, a mobile module, and option modules selected from one or more separated modules placed in a NFB performance area and one or more animal modules placed on an animal;

wherein the user module is equipped with: a set of electroencephalographic (EEG) electrodes for brainwave recording, an EEG amplifier, a data processing unit that transforms EEG signals to electronic information suitable for a wireless transfer, a pairing unit that enables connectivity with other pairing units, and an ultrasonic speaker for communication with the animal;

wherein the mobile module is equipped with a data processing unit that processes received EEG signals of one or more subjects, a pairing unit that enables connectivity with other pairing units; an animal training unit, a control unit, and an internet connection with a data cloud all connected with the data processing unit;

wherein said each option module is equipped with a corresponding data processing unit, a pairing unit, and an ultrasonic speaker for communication with an animal;

wherein the neurofeedback training on the subject is performed by the system in which said feedback chain consists of the steps:

A followed by B followed by C followed by D followed by A, where the steps include:

A. real time recording of the subject's EEG performed by the user module and forwarded to the mobile module by using their respective paired units;

B. analytics of the signal recorded in the step A performed by the data processing unit of the mobile module, and algorithmic decision making about the stimulation form for the subject whose EEG signal has been recorded;

C. forwarding the stimulation form for the subject determined in the step B towards the animal; and D. performing an action by the animal, triggered by the stimulation, which provides a stimulus to the subject exposed to the neurofeedback training of the step A;

wherein the used animal species are previously trained canine species or dolphin species, susceptible to the ultrasound, which are the only source of visual, tactile, or auditory stimulus to the subject;

wherein the information needed for the animal performance, the animal performance creating the stimulus for the subject, is forwarded in the form of a coded ultrasonic signal via one or more ultrasonic speakers simultaneously, placed on one or more of the modules selected from: the user module, the one or more separated modules; and the one or more animal modules; and wherein all of said modules are paired with the mobile module.

2. The method according to the claim 1, wherein the mobile module is wearable and situated on the subject and is optionally merged with the user module over which any changes to the NFB training, monitoring and intervention are performed via the Internet connection with the data cloud.

3. The method according to claim 1, wherein the pairing units are short-range communication units.

4. The method according to claim 1, wherein in order to provide communication in the step C, the ultrasonic speaker that emits ultrasonic signals to the animal is placed in the user module.

5. The method according to claim 1, wherein in order to provide communication in the step C, the ultrasonic speaker that emits ultrasonic signals to the animal is placed in the animal module that is noninvasively placed on the animal in the form of collar or a patch; and wherein the mobile module controls the ultrasonic signal from the ultrasonic speaker.

6. The method according to claim 1, wherein in order to provide communication in the step C, the ultrasonic speaker is placed in a separate module placed in the space; and wherein the mobile module controls the ultrasonic signal from the ultrasonic speaker.

7. The method according to claim 1, wherein the link between the mobile module and the option module and ultrasonic speakers of option modules are used to train the selected animals.

8. The method according to claim 1, wherein one or more mobile modules simultaneously process information from the step A for multiple users in order to control multiple animals in a way that each animal is trained for a different set of ultrasonic commands, enabling simultaneous independent NFB trainings in the same space without interference.

9. A communication system for conducting NFB training on the subject that includes the animal species, wherein the communication system comprises means for performing the method according to claim 1.

10. The communication system for conducting NFB training on the subject according to claim 9, wherein the user module and the mobile module combined make one new module without the control unit, wherein the control of said one new module is conducted exclusively by means of the data cloud, and wherein said one new module can be paired with any of said option modules.

* * * * *